(12) United States Patent
Capaldi et al.

(10) Patent No.: US 6,649,750 B1
(45) Date of Patent: Nov. 18, 2003

(54) PROCESS FOR THE PREPARATION OF OLIGONUCLEOTIDE COMPOUNDS

(75) Inventors: Daniel C. Capaldi, Encinitas, CA (US); Vasulinga T. Ravikumar, Carlsbad, CA (US); Douglas L. Cole, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/477,878

(22) Filed: Jan. 5, 2000

(51) Int. Cl.$^7$ ............................................... C07H 21/00
(52) U.S. Cl. .................................. 536/25.31; 536/25.34
(58) Field of Search ............................ 536/23.31, 25.34

(56) References Cited

U.S. PATENT DOCUMENTS

| | | | | |
|---|---|---|---|---|
| 4,430,229 A | * | 2/1984 | Yamawaki et al. | ......... 210/692 |
| 5,886,177 A | * | 3/1999 | Cook et al. | ................. 544/224 |
| 6,169,177 B1 | * | 1/2001 | Manoharan et al. | ..... 536/25.31 |

FOREIGN PATENT DOCUMENTS

| | | | |
|---|---|---|---|
| JP | 53-133 283 | * | 11/1978 |
| JP | 62-101 690 | * | 3/1987 |
| JP | 63-066 195 | * | 3/1988 |
| JP | 63-035 640 | * | 7/1988 |

OTHER PUBLICATIONS

Winberg et al., "Tetraaminoethylenes," *Journal of the American Chemical Society*, 87(9), 2065–2066 (May 5, 1965).*

Hoffman, "Reactions of Electron Rich Olefins," *Angewandte Chemie, Internationl Edition*, 7(10), 754–765 (Oct. 1968).*

Wiberg, "Tetraaminoethylenes as Strong Electron Donors," *Angewandte Chemie, International Edition*, 7(10), 766–779 (Oct., 1968).*

Beaucage et al., "Deoxynucleoside Phosphoramidites—A New Class of Key Intermediates for Deoxypolynucleotide Synthesis," *Tetrahedron Letters*,22(20), 1859–1862 (1981).*

McBride et al., "An Investigation for Several Deoxynucleoside Phosphoramidites Useful for Synthesizing Deoxyoligonucleotides," *Tetrahedron Letters*, 24(3), 245–248 (1983).*

Doorman et al., "Synthesis of Oligodeoxynucleotides and Oligodeoxynucleotide Analogs Using Phosphoramidite Intermediates," *Tetrahedron*, 40(1), 95–102 (1984).*

Köster et al., "Polymer Support Oligonucleotide Synthesis—XV," *Tetrahedron*, 40(1), 103–112 (1984).*

Barbato et al., "A Polymer–Necleotide Linkage Useful for the Solid Phase Synthesis of Cyclic Oligonucleotides," *Tetrahedron*, 45 (14), 4523–4536 (1989).

Barbato et al., "Solid Phase Synthesis of Cyclic Oligodeoxyribonucleotides," *Tetrahedron Letters*, 28 (46), 5727–5728 (1987).

DeNapoli et al., A New Solid–Phase Synthesis of Oligonucleotides 3'—Conjugated with Peptides, *Bioorganic & Medicinal Chemistry*, 7, 395–400 (1999).

Waldvogel et al., "Nucleotides LV. Synthesis and Application of a Novel Linker for Solid–Phase Synthesis of Modified Oligonucleotides," *Helvetica Chimica Acta*, 81, 46–58 (1998).

Hayakawa, Y., et al., "The allylic protection method in solid–phase oligonucleotide synthesis. An efficient preparation of solid–anchored DNA oligmers," *J. Am. Chem. Soc.*, 1990, 112, 1691–1696.

EPO Supplementary European Search Report dated Dec. 9, 2002 (EP 00 98 8435).

Dorman, M.A., et al., "Synthesis of oligodeoxynucleotides and oligodeoxynucleotide analogs using phosphoramidite intermediates," *Tetrahedron Letters*, 1984, 40(1), 95–102.

Koster, H., et al., "Polymer support oligonucleotide synthesis—XV; Synthesis of oligodeoxynucleotides on controlled pore glass (CPG) using phosphate and a new phosphate trimester approach," *Tetrahedron Letters*, 1984, 40(1), 103–112.

PCT Written Opinion dated Dec. 27, 2002 (PCT/US00/35612).

* cited by examiner

Primary Examiner—James O. Wilson
Assistant Examiner—Lawrence E Crane
(74) Attorney, Agent, or Firm—Woodcock Washburn LLP

(57) ABSTRACT

Synthetic processes are provided wherein high purity oligomers are prepared using support bound phosphoramidite protocols starting with a nucleoside or larger synthon linked to a support media through a nucleosidic heterocyclic base moiety. Intermediates undergoing depurination at the support linkage site are removed during the wash cycle. Also provided are compositions useful in such processes.

57 Claims, 1 Drawing Sheet

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
```

<400> SEQUENCE: 1
gcccaagctg gcatccgtca                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
tccgtcatcg ctcctcaggg                                           20

PROCESS FOR THE PREPARATION OF OLIGONUCLEOTIDE COMPOUNDS

FIELD OF THE INVENTION

The present invention is directed to methods of synthesizing high purity oligomeric compounds. The methods are directed to support bound syntheses where the attachment to the support is from a nucleosidic heterocyclic base moiety. More particularly the present methods provide for the preparation of higher purity oligomers having reduced levels of full length byproducts containing abasic sites.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomers to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous well-known protocols for coupling nucleosides through phosphorous-containing covalent linkages to produce oligonucleotides of defined sequence. One of the most routinely used protocols is the phosphoramidite protocol (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein; and The synthesis of Modified Oligonucleotides by the Phosphoramidite Approach and their applications, Beaucage, S. L.; Iyer, R. P., *Tetrahedron*, 1993, 49, 6123–6194 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

Phosphoramidites are commercially available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.).

The synthesis of oligonucleotides has classically involved obtaining a desired product which was in itself a challenge. The synthesis of oligonucleotides has more recently evolved to the point that routine syntheses are being performed on kilogram scale. Moving forward the next step is the synthesis of oligonucleotides and analogs on ton scale. The evolution of oligonucleotide synthetic techniques toward large scale is requiring a reevaluation of each aspect of the synthetic process.

One such aspect is the site of attachment of the growing oligonucleotide to a support media. The site of attachment of the first nucleoside to the solid support can have profound affects on certain impurities that are routinely found to be present in the purified oligomeric compounds ultimately isolated. During standard coupling reactions a growing oligomer is repeatedly subjected to a variety of reaction conditions. For example standard phosphoramidite synthesis conditions include deprotection of the 5'-hydroxyl group, activation of the phosphoramidite, coupling of the activated phosphoramidite to the 5'-hydroxyl, capping of unreacted sites and oxidation of the phosphite to a phosphotriester. Repeatedly subjecting the growing oligomer to these reactions to effect further couplings is known to cause a small degree of unwanted side reactions to occur. Certain of these are essentially transparent in that they don't lead to byproducts that will show up as impurities in the final HPLC purified oligomer. These byproducts are either removed during the wash cycles or during purification.

Oligomeric compounds are being routinely prepared on large scale for pharmaceutical use which requires high purity. These compounds are subjected to rigorous standards for purification and analysis prior to being used in for example human clinical trials. Certain byproducts are found to survive even the HPLC purification process and are very difficult to remove from the desired product. The reason for their persistence is that they are so structurally similar to the final desired product they aren't removed by standard HPLC. An especially difficult byproduct results from the cleavage of the glycosyl bond of one or more nucleosides in the oligomer. If a single glycosyl bond is cleaved creating an abasic site the resulting byproduct is identical to the final compound except for that one heterocyclic base moiety that was cleaved. This is one of the most difficult byproducts to detect and remove from the final product.

An inherent problem encountered using the support bound phosphoramidite method of oligomer synthesis is an abasic site in the final product caused by depurination of one or more of the linked nucleosides. It has been shown that certain sites are more prone e.g. more labile under these conditions to depurination than others including the 3'-terminal nucleoside and nucleosides close to the 3'-terminus. Depurination is more likely for nucleosides near the 3'-terminal because these sites are subjected to more coupling cycles. An especially labile position is a 3'-terminal purine nucleoside during treatment with an acidic reagent to remove the 5'-hydroxyl group. This lability is enhanced relative to other positions due to the electronic effects of the 5'- and 3'-substituents. The presence of an abasic site resulting from depurination or other reasons in an oligomeric compound is further known to enhance β-elimination (Toshinori et al., *Nucleic Acids Research*, 1994, 22, 4997–5003). Current attempts to reduce this risk of a 3'-abasic site in the final oligomer has been to alter the conditions of deprotecting the 5'-hydroxyl group during the first coupling.

One reaction condition that has been modified and studied with respect to depurination is the acid deprotection step. Studies have shown that the rate of depurination is decreased with lesser concentrations of weaker acids such as dichloroacetic acid as opposed to the industry standard of trichloroacetic acid (Septak, Michael, *Nucleic Acids Research*, 1996, 24, 3053–3058). Alternative nucleobase protecting groups have been used during the oligomerization process to reduce depurination (McBride et al., *J. Am. Chem. Soc.*, 1986, 108, 2040–2048; McBride, et al., *Tetrahedron Letters*, The presence of a abasic site in an oligomeric compound is further known to enhance β-elimination (Toshinori et al., *Nucleic Acids Research*, 1994, 22, 4997–5003). 1983, 24, 2953–2956).

There currently exists a need in the art for methods of synthesizing oligomeric compounds that reduce or eliminate byproducts that are not removed during standard purification.

Solid phase methods for the preparation of deoxyribooligonucleotides having 3'-peptide conjugates using a deoxycytidine attached to a solid support via the base are disclosed in Napoli et al., *Bioorganic & Medicinal Chemistry*, 1999, 7, 395–400.

Solid phase triester methodologies have been used to prepare cyclic oligodeoxynucleotides where the first deoxynucleoside attached to a polydimethylacrylamide support is attached at the base (Barbato et al., *Tetrahedron*, 1989, 45, 4523–4536; and Barbato et al., *Tetrahedron Letters*, 1987, 28, 5727–5728).

Attachment of a heterocyclic base to a solid support for oligomer synthesis using a linkage to the base has been previously reported (Waldvogel et al., *Helvetica Chimica Acta*, 1998, 81, 46–58). In a representative example an amino protecting group is used to protect the exocyclic amino functionality of a purine which is itself attached to a phosphate blocking group. The oligomerization proceeds from a purine not a nucleoside attached to a solid support.

SUMMARY OF THE INVENTION

The present invention is directed to methods for preparation of oligomers using support bound processes wherein the attachment of the growing oligomer to the support medium is through the heterocyclic base moiety of a base forming the oligomeric.

In one embodiment, methods are provided for preparing an oligomeric compound having at least one moiety of formula:

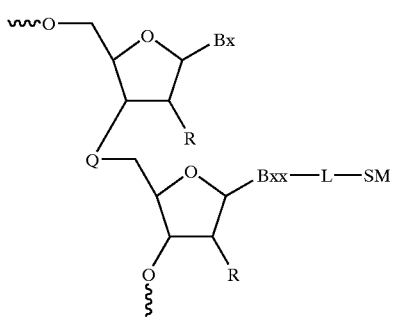

wherein:
Q is an internucleoside linkage;
Bx is an optionally blocked heterocyclic base moiety, for example, adenine, $N^6$-benzoyladenine, 2-aminoadenine, cytosine, N'-benzoylcytosine, 5-methylcytosine, $N^4$-benzoyl-5-methylcytosine, thymine, uracil, guanine or N isobutyrylguanine;
Bxx is a purine or purine analog;
each R is, independently, hydrogen or an optionally protected substituent group;
L is a bifunctional linking moiety, preferably moiety that attaches the support medium to the oligomeric compound at a heterocyclic base functional group; and
SM is a support medium;
comprising the steps of:
(a) providing a compound of formula:

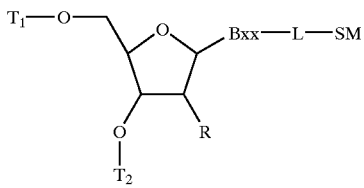

wherein:
$T_1$ is a 5'-hydroxyl protecting group; and
$T_2$ is a hydroxyl blocking group, a nucleoside, a nucleotide, an oligonucleoside, an oligonucleotide or a conjugate group, and is preferably, a hydroxyl blocking group, for example, —C(=O)$R_d$, wherein $R_d$ is $C_1$ to $C_{12}$ alkyl, such as $CH_3$, and in some preferred embodiments is base labile;
(b) deprotecting the 5'-hydroxyl protecting group to form a deprotected hydroxyl group;
(c) treating the deprotected hydroxyl group with a further compound having the formula:

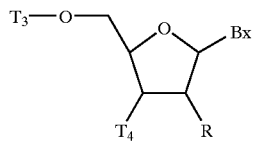

wherein:
$T_3$ is a 5'-hydroxyl protecting group, a nucleoside, a nucleotide, an oligonucleoside, an oligonucleotide or a conjugate group; and
$T_4$ is a reactive $P^{III}$ species for forming an internucleoside linkage;
and an activating agent, for example, 1-H-tetrazole, for a time and under conditions effective to form an extended oligomeric compound;

d) treating the extended oligomeric compound with a capping agent to form a capped compound;
e) treating the capped compound with an oxidizing agent, for example, oxaziridine, preferably, 10-camphorsulphonyl oxazaridine, 2-phenylsulphonyl-3-phenyl oxazaridine, 2-(phenyl sulphonyl)-3-(3-nitrophenyl)oxazaridine, or 8,8-dihalo-10-camphorsulphonyl oxazaridine; and
f) optionally repeating steps b through e one or more additional cycles to form the oligomeric compound.

In some preferred embodiments, the oligomeric compound is further treated with a reagent effective to form a deblocked oligomeric compound, for example, a basic solution such as concentrated ammonium hydroxide. In some preferred embodiments, the reagent is effective to cleave the oligomeric compound from the support medium.

In other preferred embodiments, the deblocked oligomeric compound is further treated with a reagent effective to cleave the oligomeric compound from the support medium.

In preferred embodiments of the present invention, each substituent group that is defined by R is, independently, hydroxyl, $C_1$–$C_{20}$ alkyl, $C_2$–$C_{20}$ alkenyl, $C_2$–$C_{20}$ alkynyl, halogen, amino, thiol, keto, carboxyl, nitro, nitroso, nitrile, trifluoromethyl, trifluoromethoxy, O-alkyl, O-alkenyl, O-alkynyl, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
or each substituent group has one of formula I or II:

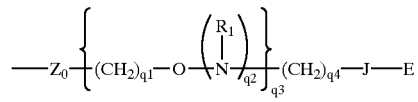
I

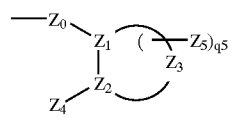
II wherein:
$Z_0$ is O, S or NH;
J is a single bond, O or C(=O);
E is $C_1$–$C_{10}$ alkyl, $N(R_1)(R_2)$, $N(R_1)(R_5)$, $N=C(R_1)(R_2)$, $N=C(R_1)(R_5)$ or has one of formula III or IV;

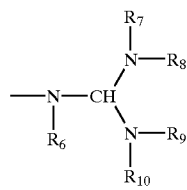
III

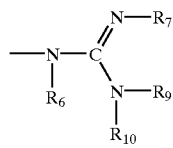
IV each $R_6$, $R_7$, $R_8$, $R_9$ and $R_{10}$ is, independently, hydrogen, $C(O)R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$, is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—$L_1$,

T is a bond or a linking moiety;

$L_1$ is a chemical functional group, a conjugate group or a solid support material;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$ guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and $L_1$, together, are a chemical functional group, for example, a primary or secondary amino group;

each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;

$R_5$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

In some preferred embodiments, the oligomeric compound comprises from about 5 to about 50 monomer subunits, preferably 10 to about 30 monomer subunits, and more preferably comprises from about 15 to 25 monomer subunits.

In particularly preferred embodiments of the present invention oligomeric compounds of the following formula are prepared:

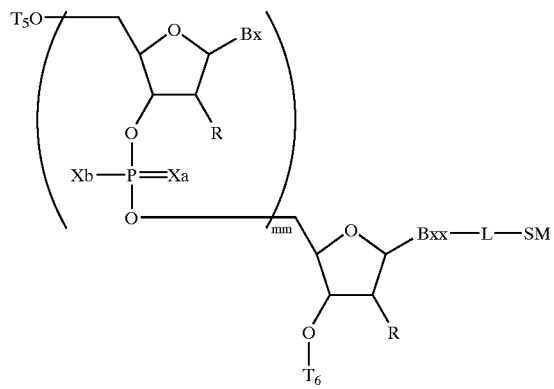

wherein:

mm is from about 5 to 50, preferably from about 10 to 30 and more preferably, from about 15 to 25;

$T_5$ is H, a hydroxyl blocking group, a nucleoside, an oligonucleoside, a nucleotide an oligonucleotide or a conjugate group;

$T_6$ is H, a hydroxyl protecting group, a nucleoside, an oligonucleoside, a nucleotide an oligonucleotide or a conjugate group;

each Xa is, independently, O or S;

each Xb is, independently, OH, SH or $NR_aR_b$;

each $R_a$ and $R_b$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is hydroxyl, amino, alkoxy, carboxy, benzyl, phenyl, nitro, thiol, thioalkoxy, halogen, alkyl, aryl, alkenyl or alkynyl;

wherein $T_1$, Bxx, Bx, R, L, and SM are defined as above; comprising the steps of:

(a) providing a compound of the formula:

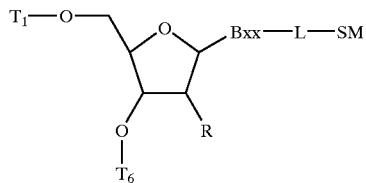

(b) deprotecting said 5'-hydroxyl protecting group to form a deprotected hydroxyl group;

(c) treating said deprotected hydroxyl group with a further compound having the formula:

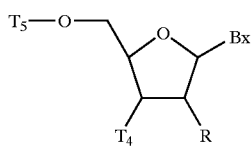

wherein:

T$_4$ is a phosphoramidite;

and an activating agent for a time and under conditions effective to form an extended oligomeric compound;

d) treating said extended oligomeric compound with a capping agent to form a capped compound;

e) treating said capped compound with an; and f) optionally repeating steps b through e one or more times to form said oligomeric compound.

Figure 1:
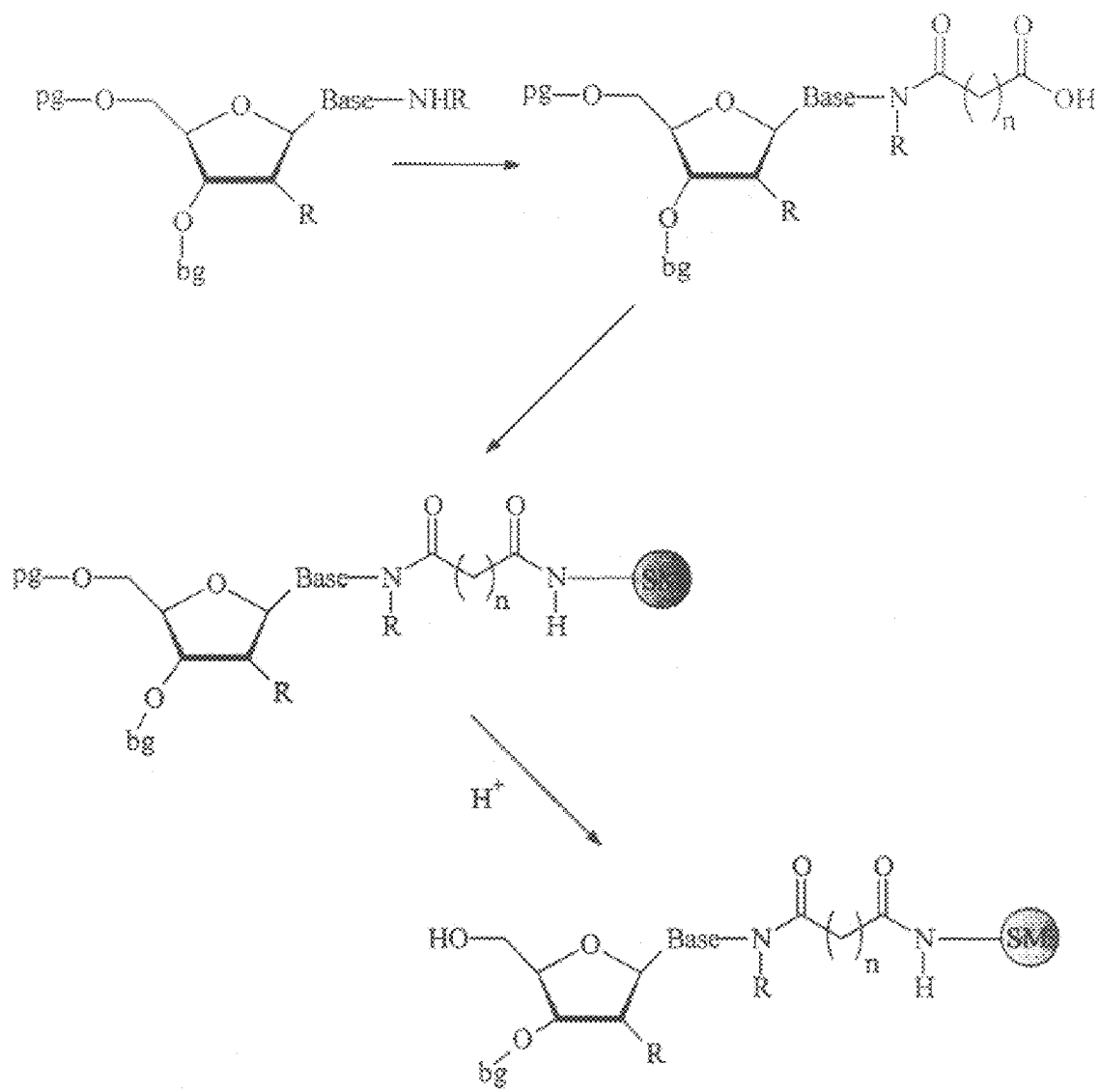
FIG. 1 shows attachment of a nucleoside to a support medium via the heterocyclic base moiety.

The present invention provides methods for the preparation of oligomeric compounds using support bound methodologies. More particularly the methods provide for eliminating unwanted byproducts that are routinely found in the final purified oligomeric compound. Such byproducts can have the same composition as the final oligomeric compound with the exception that at least one site is an abasic site. The methods are particularly useful for the preparation of oligomeric compounds having uniform or mixed phosphite, phosphodiester, phosphorothioate, or phosphorodithioate internucleotide linkages. The present invention also provides compositions useful in the preparation of such oligomeric compounds.

The methods of the present invention are especially useful for removing undesired oligomeric compounds having an abasic site at the 3'-end during the synthesis of a desired oligomer. A desired oligomer having a labile nucleoside at or near the 3'-end is prepared having that nucleoside attached to the support media by a linking group to the heterocyclic base rather than to the sugar. The nucleoside or larger synthon is elongated using preferably phosphoramidite protocols until the desired oligomer is prepared. Any cleavage of the glycosyl bond on the labile nucleoside will result in a heterocyclic base remaining attached to the support medium and the corresponding cleaved compound in solution. This methodology allows for the removal of abasic byproducts at standard washing cycles using standard support bound synthetic protocols.

In a preferred embodiment of the invention a first protected nucleoside is linked using a bifunctional linking group to a support medium through an exocyclic amino group present on the heterocyclic base of the nucleoside, see for example, FIG. 1 where the base is equal to purine or purine analog; R is H, $C_1$–$C_8$ alkyl, acyl, aryl or aralkyl; pg is an acid labile protecting group, bg is a base labile blocking group; n is from 4 to 10 and SM is a support medium. This support bound nucleoside is iteratively elongated using standard phosphoramidite protocols to a desired length and sequence (Protocols For Oligonucleotides And Analogs, Agrawal, S., ed., Humana Press, Totowa, N.J., 1993; *Oligonucleotides And Analogues A Practical Approach*, Eckstein, F. Ed., IRL Press, N.Y., 1991). Synthesis of oligomeric compounds is typically performed using automated synthesizers available from numerous sources such as for example Applied Biosystems (Foster City, Calif.). Additional methods for support bound synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

The phosphoramidite method utilizes a phosphoramidite monomer which is reacted with a free hydroxyl on a growing oligomer chain to produce an intermediate phosphite $P^{III}$ compound. The intermediate $P^{III}$ compound is subsequently oxidized to the $P^V$ state using standard methods. This technique is commonly used for the synthesis of several types of linkages including but not limited to phosphodiesters, phosphorothioates, and phosphorodithioates. In one embodiment the coupling step is performed under anhydrous conditions in the presence of an activating agent such as, for example, 1H-tetrazole, 5-(4-nitrophenyl)-1H-tetrazole, or diisopropylamino tetrazolide.

To eliminate unreacted intermediates at each coupling cycle it is preferable to perform a capping step, either prior to or after oxidation or sulfurization of the phosphite triester, thiophosphite triester, or dithiophosphite triester. Such a capping step is generally known to be beneficial by preventing shortened oligomer chains by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Further treatment with an acid removes the 5'-hydroxyl protecting group, and thus transforms the support bound oligomer into a further reactive compound that can participate in the next synthetic iteration by reaction with a further phosphoramidite. This process is repeated until an oligomer of desired length is produced. In a preferred embodiment of the invention the resulting oligomer is protected at the 5'-end with an acid labile protecting group, blocked at reactive sites either on or attached to sugars and/or heterocyclic base moieties with base labile blocking groups, blocked at phosphorus by one or more phosphorus blocking groups and is attached to a support media by a heterocyclic base moiety where such attachment is preferably via a bifunctional linker such as a bifunctional $C_4$ to $C_{25}$ linking group. Preferred 3'-O-protecting groups for the 3'-terminus during oligomerization, as this site is not attached to a support medium, includes groups of the formula —C(=O)(CH$_2$)$_n$—CH$_3$ where n is from 0 to 11.

As used herein the term protecting group includes groups that protect reactive sites that need to be deprotected and treated with further reagents and activated monomers during the course of oligomerization such as a 5'-hydroxyl group. As used herein the term blocking group is meant to include groups that block reactive sites during oligomerization reactions. Such groups are removed by treatment with a deblocking agent after the oligomerization is complete thus allowing the incorporation of a variety of reactive functionalities at specific sites throughout the final oligomeric compound.

Post synthesis processing of the oligomeric compound generally requires deblocking of the blocking groups, cleavage of the oligomer from the support medium and deprotection of the protecting group on the last remaining 5'-hydroxyl group. Deblocking and cleaving the resultant oligomer is preferably by treatment with a reagent that allows deblocking of all the blocking groups without cleaving the oligomeric compound from the support. This strategy allows for the removal of the compounds resulting from the deblocking procedures by standard rinsing of the support bound oligomer. Further treatment with a base under more vigorous conditions such as a solution having a higher pH or increased temperature or increasing the time of exposure will effect cleavage of the oligomer from the solid support. The deblocking and cleavage can easily be performed in one step if desired. Treatment of the 5'-hydroxyl protecting group with an acidic solution at any time before or after general deblocking or cleavage yields the free 5'-hydroxyl group.

In a preferred deblock/cleavage scheme the solid support bound, fully blocked oligomer is first treated with a basic reagent effective to remove blocking groups on phosphorus, sugar and heterocyclic base positions. Many reagents can selectively remove most blocking groups without cleavage of the oligomer from the support media. Representative reagents for selectively deblocking without simultaneous cleavage include, but are not limited to, DBU and triethylamine in ethanol.

The oligomer is next treated with a reagent effective to cleave the covalent linkage to the support media. Such treatment will also remove blocking groups that were not removed under milder conditions described above. A preferred reagent for this cleavage is aqueous ammonia. Removal of the 5'-hydroxyl protecting group can be effected prior to or after purification by treatment with an acidic solution. One advantage of purifying the oligomer with the hydroxyl protecting group on is that it aids in the purification process. The elution of the oligomer is slowed down, thus allowing impurities to be eluted first when doing HPLC purification using, for example, a $C_{18}$ reverse phase column.

In one aspect of the present invention the deblocking and simultaneous cleavage of a desired oligomeric compound following synthesis is accomplished in one step using a solution of ammonium hydroxide. An oligomeric compound is prepared using support bound protocols is treated with $NH_4OH$ (30%) for 15 hours at 60° C., filtered, rinsed with ethanol/water (1/1, v/v), and the combined solutions are evaporated to dryness under vacuum. The residue is dissolved in water (50 mL).

The purification of oligonucleotides is generally by reversed phase high performance liquid chromatography (RP-HPLC) performed on a Waters Nova-Pak C18 column (3.9×300 mm) using a Waters HPLC system (600E System Controller, 996 Photodiode Array Detector, 717 Autosampler). For analysis an acetonitrile (A)/0.1M triethylammonium acetate gradient is used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR(DMT-off) 10–11 min, tR(DMT-on) 14–16 min. The DMT-on fractions are collected and are evaporated in vacuum, redissolved in water and the DMT group removed as described below.

Removal of the final hydroxyl protecting group from the 5'-hydroxyl group is generally performed by treatment with an acidic solution such as acetic acid. The oligomeric compound is treated with the acidic solution for about 30 minutes at room temperature. The mixture is further treated with sodium acetate and cold ethanol followed by vortexing and cooling with dry ice. The precipitate is centrifuged, separated, washed and dried to give the final deprotected product.

In the context of this invention, the terms "oligomer" and "oligomeric compound" refer to a plurality of naturally-occurring or non-naturally-occurring nucleosides linked together in a specific sequence. The terms "oligomer" and "oligomeric compound" include oligonucleotides, oligonucleotide analogs, oligonucleosides and chimeric oligomeric compounds where there are more than one type of internucleoside linkages dividing the oligomeric compound into regions. Oligomeric compounds are typically structurally distinguishable from, yet functionally interchangeable with, naturally-occurring or synthetic wild-type oligonucleotides. Thus, oligomeric compounds include all such structures which function effectively to mimic the structure and/or function of a desired RNA or DNA strand, for example, by hybridizing to a target. Whereas the term "oligonucleotide" has a well defined meaning in the art, the term "oligomeric compound" or "oligomer" is intended to be broader, inclusive of oligomers having all manner of modifications known in the art. Gapped or chimeric compounds are disclosed in for example, U.S. Pat. No. 5,623,065, issued Apr. 22, 1997, the contents of which are incorporated herein by reference.

The current method of choice for the preparation of oligomeric compounds uses support media. A nucleoside or larger nucleosidic synthon is attached to a support medium and iteratively coupled to further nucleosides to give a final oligomeric compound. Traditional solid supports are insoluble and are routinely placed in a reaction vessel while reagents and solvents react and or wash the growing chain until cleavage frees the final oligomer. More recent approaches have introduced soluble supports including soluble polymer supports to allow controlling the phase of the support bound oligomeric compound during synthesis. This application of soluble supports is referred to in the literature as "liquid-phase methods" (Gravert et al., *Chem. Rev.*, 1997, 97, 489–510). One of the goals of liquid-phase methodology is to allow coupling reactions to occur with the growing oligomer chain soluble. Allowing the support bound growing oligomer to couple to additional activated nucleosides in solution has a definite kinetic advantage over traditional solid phase methodologies.

The term "soluble," in the context of the term "soluble support," means that a solid support can be dissolved in a preselected solvent during oligomer synthesis. After completion of synthesis, the support-bound oligomer can be isolated from the reaction mixture by precipitation, by the addition of a solvent such as an ether. Soluble supports include dendrimers, dendrons, cascade polymers, arborols and blocked copolymers.

Soluble supports may be prepared by methods well known in the art, including those disclosed in U.S. Pat. Nos. 4,435,548; 4,472,509; 4,507,466; 4,558,120; 4,568,737; 4,587,329; 4,606,907; 4,631,337; 4,634,586; 4,675,173; 4,694,064; 4,737,550; 4,824,659; 4,857,599; 4,871,779; 4,916,246; 4,980,148; 5,021,236; 5,039,512; 5,041,516; 5,136,014; and U.K. Patent Application No. GB2316941A. In a preferred embodiment the soluble support is polyethylene glycol. In another preferred embodiment the soluble support is monomethoxy polyethylene glycol. In a further preferred embodiment the soluble support is poly(N-acryloyl-morpholine).

Representative support media that are amenable to the methods of the present invention include without limitation: controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a copolymer of polystyrene/divinylbenzene available from Perceptive Biosystems. Further support media amenable to the present invention are disclosed in the two Beaucage review papers ibid.

In the context of this invention, a "heterocyclic ring system" is a cyclic compound containing at least one heteroatom such as N, O, or S. A "mixed heterocycle" is a cyclic compound containing at least two heteroatoms such as N, O or S. A "heteroaryl" compound is a heterocycle containing at least one heteroatom such as N, O or S and is not fully saturated, e.g., is in a state of partial or complete saturation. "Heteroaryl" is also meant to include fused systems including systems where one or more of the fused rings contain no heteroatoms.

Preferred heterocycles amenable to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine. A more preferred group of nitrogen heterocycles includes imidazole, pyrrole and carbazole.

A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993.

As used herein, "purine analogs" include modified purine heterocyclic base moieties such as xanthine, hypoxanthine, 2-aminoadenine, 7-methylguanine, 7-methyladenine, 6-methyl and other alkyl derivatives of adenine and guanine, 2-propyl and other alkyl derivatives of adenine and guanine, 8-halo, 8-amino, 8-thiol, 8-thioalkyl, 8-hydroxyl and other 8-substituted adenines and guanines, 8-azaguanine, 8-azaadenine, 7-deazaguanine, 7-deazaadenine, 3-deazaguanine and 3-deazaadenine. Further purine analogs amenable to the present invention include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. More preferred purine analogs have or modified to have a primary or secondary amino functionality integral with or exocyclic to the purine ring system.

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. Pat. No. 6,016,348, also herein incorporated by reference.

The attachment of conjugate groups to oligomers is well documented in the prior art. The oligomeric compounds of the inventioA can include conjugate groups covalently bound to functional groups such as primary or secondary hydroxyl groups. In a preferred embodiment conjugate groups are attached at one of the 5' or 3'-terminal ends of oligomers of the invention. Conjugate groups of the invention include intercalators, reporter molecules, polyamines, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 (now U.S. Pat. No. 6,153,737, issued Nov. 28, 2000), U.S. Pat. No. 5,578,718, issued Jul. 1, 1997, and U.S. Pat. No. 5,218,105. Each of the foregoing is commonly assigned with this application.

Preferred conjugate groups amenable to the present invention include lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), adamantane acetic acid (Manoharan et al., *Tetrahedron Lett.*, 1995, 36, 3651), a palmityl moiety (Mishra et al., *Biochim. Biopllys. Acta*, 1995, 1264, 229), or an octadecylamine or hexylamino-carbonyl-oxycholesterol moiety (Crooke et al., *J. Pharmacol. Exp. Ther.*, 1996, 277, 923).

Other groups that can be attached to oligomeric compounds of the invention to modify antisense properties include RNA cleaving complexes, pyrenes, metal chelators, porphyrins, alkylators, hybrid intercalator/ligands and photo-crosslinking agents. RNA cleavers include o-phenanthroline/Cu complexes and $Ru(bipyridine)_3^{2+}$ complexes. The $Ru(bpy)_3^{2+}$ complexes interact with nucleic acids and cleave nucleic acids photo-chemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

Hybrid intercalator/ligands include the photonuclease/intercalator ligand 6-[[[9-[[6-(4-nitrobenzamido)hexyl] amino]acridin-4-yl]carbonyl]amino]hexanoyl-pentafluorophenyl ester. This compound has two noteworthy features: an acridine moiety that is an intercalator and a p-nitro benzamido group that is a photonuclease.

Photo-crosslinking agents include aryl azides such as, for example, N-hydroxy-succiniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation, They also crosslink with carrier proteins (such as KLH or BSA), raising antibody against the oligonucleotides.

Chiral internucleoside linkages including phosphorothioate internucleoside linkages (Rp and Sp) are amenable to the methods of the present invention. Oligonucleotides that have chiral Sp phosphorothioate internucleotide linkages at the 3'-terminus are disclosed in International Publication Number WO 99/05160, published Feb. 4, 1999. The solid-phase stereoselective synthesis of 2'-O-methyl oligoribonucleoside phosphorothioates has been reported using bicyclic oxaza-phospholidines (Guo et al., *Bioorganic & Medicinal Chemistry Letters*, 1998, 8, 2539–2544). Methods for the enzymatic synthesis of oligonucleotides are disclosed by Hyman in U.S. Pat. No. 5,602,000 issued Feb. 11, 1997, entitled "Method for Enzymatic Synthesis of Oligonucleotides". Enzymes are also being used to prepare random libraries (aptamers) having both phosphodiester and phosphorothioate internucleoside linkages where the phosphorothioate internucleoside linkages are chiral Rp linkages (King et al., *Biochemistry*, 1998, 37, 16489–16493).

One approach to forming chiral phosphorothioate internucleoside linkages uses chiral auxiliary protecting groups as part of their activated phosphorus groups. After each addition the chiral internucleoside linkage is sulfurized using for example Beaucage reagent. As used herein the term "chiral auxiliary" is meant to include groups that function to provide chirality to internucleoside phosphorus linkages during the course of the synthesis of oligomeric phosphorothioates. Chiral auxiliaries will give either Sp or Rp chirality for the respective internucleoside linkage in the final oligomeric compound.

Vitamins can also be attached to oligomeric compounds of the invention to improve properties such as absorption and distribution. Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), retinol-binding protein (RBP), and cellular retinol-binding protein (CRBP). These proteins, which have been found in various parts of the human body, have molecular weights of approximately 15 kD. They have specific interactions with compounds of vitamin-A family, especially, retinoic acid and retinol.

The methods of the present invention can include appropriate activated phosphorus groups such as activated phosphate groups and activated phosphite groups. As used herein, the terms activated phosphate and activated phosphite groups refer to activated monomers or oligomers that are reactive with a hydroxyl group of another monomeric or oligomeric compound to form a phosphorus-containing internucleotide linkage. Such activated phosphorus groups contain activated phosphorus atoms in $P^{III}$ or $P^V$ valency states. Such activated phosphorus atoms are known in the art and include, but are not limited to, phosphoramidite, H-phosphonate and phosphate triesters. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

The term "nucleoside" as used in connection with this invention refers to a monomeric unit made up of a heterocyclic base moiety joined to a sugar moiety or sugar mimetic through a glycosyl linkage. The term "nucleotide" refers to a nucleoside having a phosphate group on its 3' or 5' sugar hydroxyl group.

As used herein, the term "phosphorus blocking group" refers to a group that is initially bound to the phosphorus atom of a phosphoramidite. The phosphorus blocking group functions to protect the phosphorus containing internucleotide linkage or linkages during, for example, solid phase oligonucleotide synthetic regimes. Treatment of the internucleotide linkage or linkages that have a phosphorus blocking group thereon with a deblocking agent, such as aqueous ammonium hydroxide, will result in the removal of the phosphorus blocking group and leave a hydroxyl or thiol group in its place.

There are many phosphorus blocking groups known in the art which are useful in the present invention including, but not limited, to β-cyanoethyl, diphenylsilylethyl, δ-cyanobutenyl, cyano p-xylyl (CPX), methyl-N-trifluoroacetyl ethyl (META) and acetoxy phenoxy ethyl (APOE) groups. Phosphorus protecting groups are further described in Beaucage, S. L. and Iyer, R. P., *Tetrahedron*, 1993, 49, 1925–1963; Beaucage, S. L. and Iyer, R. P., *Tetrahedron*, 1993, 49, 10441–10488; and Beaucage, S. L. and Iyer, R. P., *Tetrahedron*, 1992, 48, 2223–2311. Representative U.S. patents that teach the preparation of phosphorus protecting groups and their incorporation into phosphoramidite compounds include, but are not limited to, U.S. Pat. Nos. 5,783,690; 5,760,209; 5,705621; 5,614,621; 5,453, 496; 5,153,319; 5,132,418; 4,973,679; 4,725,677; 4,668, 777; 4,500,707; 4,458,066; 4,415,732; and Re. 34,069, the entire contents of each of which are herein incorporated by reference.

Oligomeric compounds of the present invention include nucleosides having modified sugar and or heterocyclic base moieties. One such modification is the addition of a substituent group. Substituent groups can modify properties of the oligomeric compounds such as for example chemical or pharmacological properties. Although more commonly used at a sugar position, preferably the 2'-position, a substituent group can also be attached to a heterocyclic base moiety. Substituent groups can be covalently attached to purines at the N2 or N6 position and pyrimidines at the N4 or C5 position.

A representative list of substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkylamino, O-alkylalkoxy, O-alkylaminoalkyl, O-alkyl imidazole, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249). Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, (now U.S. Pat. No. 6,166,197, issued on Dec. 26, 2000) entitled Oligomeric Compounds having Pyrimidine Nucleotide(s) with 2' and 5' Substitutions, hereby incorporated by reference in its entirety.

Additional substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further substituent groups have one of formula I or II:

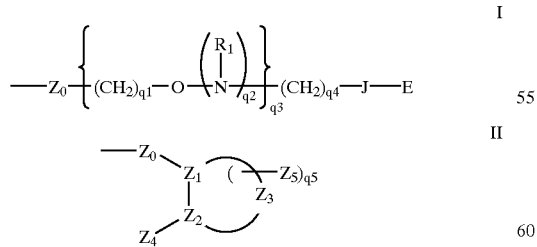

wherein:
  $Z_0$ is O, S or NH;
  J is a single bond, O or C(=O);
  E is $C_1$–$C_{10}$ alkyl, N($R_1$)($R_2$), N($R_1$)($R_5$), N=C($R_1$)($R_2$), N=C($R_1$)($R_5$) or has one of formula III or IV;

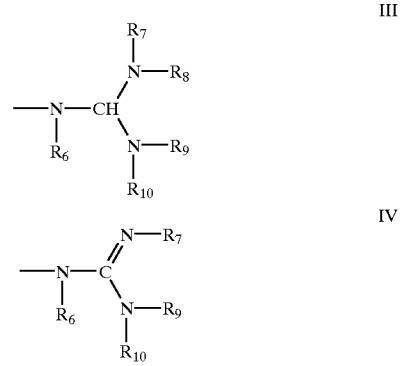

each $R_6$, $R_7$, $R_8$, $R_9$ and $R_{10}$ is, independently, hydrogen, C(O)$R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
  or optionally, $R_7$ and $R_8$, together form a phthalimido moiety with the nitrogen atom to which they are attached;
  or optionally, $R_9$ and $R_{10}$, together form a phthalimido moiety with the nitrogen atom to which they are attached;
  each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
  $R_5$ is T—L,
  T is a bond or a linking moiety;
  L is a chemical functional group, a conjugate group or a solid support material;
  each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is O$R_3$, S$R_3$, NH$_3^+$, N($R_3$)($R_4$), guanidino or acyl where said acyl is an acid amide or an ester;
  or $R_1$ and $R_2$, together, are a nitrogen protecting group or are joined in a ring structure that optionally includes an additional heteroatom selected from N and O;
  or $R_1$, T and L, together, are a chemical functional group;
  each $R_3$ and $R_4$ is, independently, H, $C_1$–$C_{10}$ alkyl, a nitrogen protecting group, or $R_3$ and $R_4$, together, are a nitrogen protecting group;
  or $R_3$ and $R_4$ are joined in a ring structure that optionally includes an additional heteroatom selected from N and O;
  $Z_4$ is OX, SX, or N(X)$_2$;
  each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;
  $R_5$ is H or $C_1$–$C_8$ alkyl;
  $Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

Representative substituent groups of Formula I are disclosed in U.S. Pat. No. 6,172,209, issued Jan. 9, 2001, hereby incorporated by reference in its entirety.

Representative cyclic substituent groups of Formula II are disclosed in U.S. patent application Ser. No. 09/123,108, filed Jul. 27, 1998 (now U.S. Pat. No. 6,271,358, issued Aug. 7, 2001), entitled "RNA Targeted 2'-Modified Oligonucleotides that are Conformationally Preorganized," hereby incorporated by reference in its entirety.

Particularly preferred substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, $O(CH_2)_nON[(CH_2)_nCH_3)]_2$ (where n and m are from 1 to about 10), $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocyclo-alkaryl, aminoalkylamino, poly-alkylamino and substituted silyl. Another particularly preferred modification includes 2'-methoxy-ethoxy (2'-O—$CH_2CH_2OCH_3$ or 2'-MOE, Martin et al., Helv. Chim. Acta, 1995, 78, 486). A further preferred substituent group -is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, also identified by attorney docket number ISIS-3993, entitled Aminooxy-Functionalized Oligomers and Methods for Making Same.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5'-position at a 5'-terminus. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,05315,639,873; 5,646,265; 5,658,873; 5,670,633; and 5,700,920, certain of which are commonly owned, and each of which is herein incorporated by reference, and commonly owned U.S. Pat. No. 5,859,221, issued Jan. 12, 1999, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999.

Representative acetamido substituent groups are disclosed in U.S. Pat. No. 6,147,200, issued Nov. 14, 2000, hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999 (now published as WO 00/08044, Feb. 17, 2000; whose parent is U.S. application Ser. No. 09/130,566, filed on Aug. 7, 1998, now U.S. Pat. No. 6,043,352, issued on Mar. 28, 2000), also identified by attorney docket number ISIS-4045, hereby incorporated by reference in its entirety.

Substituent groups, cyclic and exocyclic functional groups are routinely blocked during oligomer synthesis and subsequently deblocked. In general, a blocking group renders a chemical functionality of a molecule inert to specific reaction conditions and can later be removed from such functionality in a molecule without substantially damaging the remainder of the molecule. A detailed list of blocking and protecting groups and such conditions used for their placement and removal are described in Protective Groups in Organic Synthesis, $3^{rd}$ edition, John Wiley & Sons, New York, 1999. For example, amino groups can be blocked with phthalimido, 9-fluorenylmethoxycarbonyl (FMOC), triphenyl-methylsulfenyl, t-BOC or benzyl groups. Carboxyl groups can be protected as acetyl groups. Representative hydroxyl protecting groups are described by Beaucage et al., Tetrahedron 1992, 48, 2223. Preferred hydroxyl protecting groups are acid-labile groups, such as the trityl, monomethoxytrityl, dimethoxytrityl, trimethoxytrityl, 9-phenylxanthine-9-yl (Pixyl) and 9-(p-methoxyphenyl) xanthine-9-yl (MOX). Chemical functional groups can also be "blocked" by including them in a precursor form. Thus an azido group can be considered a "blocked" form of an amine as the azido group is easily converted to the amine. Further representative protecting groups utilized in oligonucleotide synthesis are discussed in Agrawal et al., Protocols for Oligonucleotide Conjugates, Eds., Humana Press, New Jersey, 1994, Vol. 26, pp. 1–72.

As used herein, the term oligonucleoside includes oligomers or polymers containing two or more nucleoside subunits having a non-phosphorous linking moiety such as for example —$CH_2$—NH—O—$CH_2$—, —$CH_2$—$N(CH_3)$—O—$CH_2$— [known as a methylene (methylimino) or MMI backbone], —$CH_2$—O—$N(CH_3)$—$CH_2$—, —$CH_2$—N ($CH_3$)—$N(CH_3)$—$CH_2$— and —O—$N(CH_3)$—$CH_2$-$CH_2$— internucleoside linking groups. Oligonucleosides according to the invention have a plurality of monomeric subunits each with a ribofuranose moiety attached to a nucleobase through a glycosyl bond. An oligo-nucleotide/nucleoside for the purposes of the present invention is a mixed backbone oligomer having at least two nucleosides covalently bound by a non-phosphate linkage and at least one phosphorous containing covalent bond with a nucleotide, and wherein at least one of the monomeric nucleotide or nucleoside units is a 2'-O-substituted compound prepared using the process of the present invention. An oligo-nucleotide/nucleoside can additionally have a plurality of nucleotides and nucleosides coupled through phosphorous containing and/or non-phosphorous containing linkages.

As used herein, the term "alkyl" includes, but is not limited to, straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. Substituent groups include, but are not limited to, alkyl, alkenyl, alkynyl, aryl, hydroxyl, alkoxy, alcohol, benzyl, phenyl, nitro, thiol, thioalkoxy, thioalkyl, trifluoromethyl, halo, nitrile, trifluoromethoxy and azido. As used herein, the term "lower alkyl" is intended to mean an alkyl group having 10 or fewer carbons.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups.

Alkaryl groups are those in which an aryl moiety links an alkyl moiety to a core structure, and aralkyl groups are those in which an alkyl moiety links an aryl moiety to a core structure.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(=O)-alkyl. A preferred alkanoyl group is the acetyl group.

In some preferred embodiments of the present invention, a first nucleoside, dimer, trimer or larger synthon is attached to a support medium using a bifunctional linking moiety. Bifunctional linking moieties are known in the art to connect a support medium to functional groups (e.g., hydroxyl groups) of initial synthon molecules using well established protocols. Suitable bifunctional linking moieties are disclosed in, for example, *Oligonucleotides And Analogues A Practical Approach*, Eckstein, F. Ed., IRL Press, N.Y., 1991, Chapter 1, pages 1–23. Preferred bifunctional linking moieties have the formula—C(=O)—(CH$_2$)$_{nn}$—C(=O)— where nn is from 4 to 25. A more preferred range for nn is from 6 to 20 with 8 to 16 being most preferred.

Sulfurizing agents used during oxidation to form phosphorothioate and phosphorodithioate linkages include Beaucage reagent (Iyer, R. P. et. al., *J. Chem. Soc.*, 1990, 112, 1253–1254, and Iyer, R. P. et. al., *J. Org. Chem.*, 1990, 55, 4693–4699); tetraethylthiuram disulfide (Vu, H., Hirschbein, B. L., *Tetrahedron Lett.*, 1991, 32, 3005–3008); dibenzoyl tetrasulfide (Rao, M. V. et. al., *Tetrahedron Lett.*, 1992, 33, 4839–4842); di(phenyl-acetyl)-disulfide (Kamer, P. C. J., *Tetrahedron Lett.*, 1989, 30, 6757–6760); bis(O,O-diisopropoxy phosphinothioyl)disulfides (Stec et al., *Tetrahedron Lett.*, 1993, 34, 5317–5320); 3-ethoxy-1,2,4-dithiazoline-5-one (*Nucleic Acids Research*, 1996 24, 1602–1607, and *Nucleic Acids Research*, 1996 24, 3643–3644); bis(p-chlorobenzenesulfonyl)disulfide (*Nucleic Acids Research*, 1995 23, 4029–4033); sulfur, sulfur in combination with ligands like triaryl, trialkyl, triaralkyl, or trialkaryl phosphines.

Useful s used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization, the reaction is performed under anhydrous conditions with the exclusion of air, in particular oxygen, whereas in the case of oxidation the reaction can be performed under aqueous conditions.

As used herein, "polyamine" refers to a moiety containing a plurality of amine or substituted amine functionalities. Polyamines according to the present invention have at least two amine functionalities. "Polypeptide" refers to a polymer comprising a plurality of amino acids linked by peptide linkages, and includes dipeptides and tripeptides. The amino acids may be naturally-occurring or non-naturally-occurring amino acids. Polypeptides according to the present invention comprise at least two amino acids.

Preferred internucleoside linkages that can be prepared as illustrated above or following protocols well known in the art include:

phosphodiester (—O—P(O)(O)—O—);

phosphorodithioate (—O—P(S)(S)—O—);

chiral and achiral phosphorothioate (—O—P(S)(O)—O—);

phosphoramidate (—O—P(O)(NJ)—O—);

alkylphosphonate (—O—P(jj)(O)—O—), wherein jj is $C_1$–$C_{12}$ alkyl; and methylene phosphonate (—CH$_2$—P(O)(O)—O—).

Methods of the present invention may be used to routinely synthesize oligomeric compounds that are from about 5 to about 50 monomer subunits. It is more preferred that such compounds comprise from about 10 to about 30 monomer subunits, with 15 to 25 monomer subunits being particularly preferred. When used as "building blocks" in assembling larger oligomers, smaller oligomers are preferred.

Oligomeric compounds prepared using the methods of the present invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism is contacted with an oligonucleotide having a sequence that is capable of specifically hybridizing with a strand of nucleic acid coding for the undesirable protein. Treatment of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the present invention. Seemingly diverse organisms, such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 µg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.91 µg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

For therapeutic or pharmaceutical use, the oligomeric compounds of the present invention may be taken up in pharmaceutically acceptable carriers such as, for example, solutions, suspensions, tablets, capsules, ointments, elixirs and injectable compositions. The dosage administered depends upon factors such as the nature and severity of the condition, the stage of the condition, and the condition of the patient. An effective amount of oligomeric compound of the invention may be from about 10 µg/kg body weight to about 1000 µg/kg body weight.

As will be recognized, the steps of the methods of the present invention need not be performed any particular number of times or in any particular sequence. Additional objects, advantages, and novel features of this invention will become apparent to those skilled in the art upon examination of the following illustrative examples, which are not intended to be limiting.

EXAMPLES

Example 1

5'-O-DMT-N6-Phenoxyacetyl-3'-O-acetyl-2'-deoxyadenosine

To a stirred solution of 5'-O-DMT-N6-phenoxyacetyl-2'-deoxyadenosine (2 mmole) (Chemgenes Inc.) in a dichloromethane (200 mL) was added acetic anhydride (4 mmole) at room temperature. After stirring the reaction for 10–12 hours, the reaction mixture was quenched with methanol and diluted further with dichloromethane (100 mL). The crude product was washed with aqueous saturated sodium bicarbonate solution (2×100 mL), brine (100 mL) and dried ($Na_2SO_4$). Concentration of the extract afforded the crude material which upon purification by flash column chromatography afforded the desired product as a colorless amorphous solid.

Example 2

5'-O-DMT-3'-O-Acetyl-2'-deoxyadenosine

Treatment of 5'-O-DMT-N6-phenoxyacetyl-3'-O-acetyl-2'-deoxyadenosine with a solution of methanolic ammonia for a brief time (1–2 hours) followed by concentration and purification by flash silica gel column chromatography afforded the title compound as a colorless amorphous solid.

Example 3

Reaction of 5'-O-DMT-3'-O-Acetyl-2'-deoxyadenosine With Dodecanoyl Dichloride

To a stirred solution of dodecanoyl dichloride (2 mmole) in anhydrous tetrahydrofuran (50 mL) under argon was added 1H-tetrazole (6 mmole) followed by triethylamine (20 mmole). Stirring at room temperature for 1–2 hours afforded the ditetrazolide compound. The reaction mixture was filtered under anhydrous conditions into another round bottom flask and to it was added a solution of 5'-O-DMT-3'-O-acetyl-2'-deoxyadenosine (1 mmole) in anhydrous tetrahydrofuran (50 mL). After stirring for 6–8 hours, the reaction was quenched with triethylammonium bicarbonate solution (50 mL). The reaction mixture was concentrated, taken up in ethyl acetate (200 mL) and washed with brine (50 mL). Drying ($Na_2SO_4$) followed by concentration and purification

Example 4

Loading of N-Protected-5'-O-DMT-3'-O-acetyl-2'-deoxyadenosine on HL 30 Primer Solid Support Loading of the protected nucleoside was performed under the standard conditions using amino derivatized primer support purchased from Amhersham-Pharmacia Biotech. Amino derivatized HL 30 Primer support, Hunig's base (12 equiv), HBTU activator (4 equiv), the DMT dA nucleoside with the linker synthesized as above and anhydrous acetonitrile (100 mL) were taken in a round bottom flask and closed and shaken mechanically at room temperature for 6 hours. The support was then washed with acetonitrile (100 mL) and dried. Then a mixture of Cap A and Cap B solution used for oligomerization (20 mL each) was added to the support followed by a catalytic amount of 4-dimethylaminopyridine and shaken overnight mechanically. The support was washed with acetonitrile (200 mL), anhydrous DMF (100 mL), methanol (100 mL) and finally with anhydrous ether (200 mL) The support was finally dried thoroughly and then tested for loading (loading=80 $\mu$mol/gram).

Example 5

Synthesis of Fully-modified 5'-d(GCC-CAA-GCT-GGC-ATC-CGT-CA)-3' (SEQ ID NO:1) Phosphorothioate 20-mer The synthesis of SEQ ID NO: 1 was performed on a Pharmacia OligoPilot I1 Synthesizer on a 160 $\mu$mole scale using the cyanoethyl phosphoramidites obtained from Pharmacia and Pharmacia's HL 30 primer support loaded with DMT-N6bz-dA nucleoside (support linked to 3'-position). Detritylation was performed using 3% dichloroacetic acid in toluene (volume/volume). Activation of phosphoramidites was done with a 0.4M solution of 1H-tetrazole in acetonitrile. Sulfuirization was performed using a 0.2M solution of phenylacetyl disulfide in acetonitrile:3-picoline (1:1 v/v) for 2 minutes. At the end of synthesis, the support was washed with a solution of triethylamine in acetonitrile (1:1, v/v) for 12 h, cleaved, deprotected and purified by reverse phase HPLC in the usual manner.

Example 6

Synthesis of Fully-modified 5'-d(GCC-CAA-GCT-GGC-ATC-CGT-CA)-3' (SEQ ID NO:1) Phosphorothioate 20-mer Using dA Functionalized Solid Support Linked Through the N6 Amino Group The synthesis of the above sequence was performed using a Pharmacia OligoPilot I1 Synthesizer on a 140 $\mu$mole scale using cyanoethyl phosphoramidites obtained from Pharmacia and Pharmacia's HL 30 primer support loaded with 5'-O-DMT-3'-O-acetyl-N-dodecanoyl-dA nucleoside. Detritylation was performed using 3% dichloroacetic acid in toluene (volume/volume). Activation of phosphoramidites was done with a 0.4M solution of 1H-tetrazole in acetonitrile. Sulfurization was performed using a 0.2M solution of phenylacetyl disulfide in acetonitrile:3-picoline (1:1 v/v) for 2 minutes. At the end of synthesis, the support was washed with a solution of triethylamine in acetonitrile (1:1, v/v) for 12 h, cleaved, deprotected and purified by reverse phase HPLC in the usual manner.

Example 7

5'-O-DMT-N2-Phenoxyacetyl-3'-O-acetyl-2'-deoxyguanosine

To a stirred solution of 5'-O-DMT-N6-phenoxyacetyl-2'-deoxyguanosine (2 mmole) (Chemgenes Inc.) in a dichloromethane (200 mL) was added acetic anhydride (4 mmole) at room temperature. After stirring the reaction for 10–12 hours, the reaction mixture was quenched with methanol and diluted further with dichloromethane (100 mL). The crude product was washed with aqueous saturated sodium bicarbonate solution (2×100 mL), brine (100 mL) and dried ($Na_2SO_4$). Concentration of the extract afforded the crude material which upon purification by flash column chromatography afforded the desired product as a colorless amorphous solid.

Example 8

5'-O-DMT-3'-O-Acetyl-2'-deoxyguanosine

Treatment of 5'-O-DMT-N6-phenoxyacetyl-3'-O-acetyl-2'-deoxyguanosine with ammonia for a brief time followed by workup and purification by flash column chromatography afforded the title compound as a colorless product.

Example 9

Reaction of 5'-O-DMT-3'-O-Acetyl-2'-deoxyguanosine With Dodecanoyl Dichloride To a stirred solution of dodecanoyl dichloride (2 mmole) in anhydrous tetrahydrofuran (50 mL) under argon was added 1H-tetrazole (6 mmole) followed by triethylamine (20 mmole). Stirring at room temperature for 1–2 hours afforded the ditetrazolide compound. The reaction mixture was filtered under anhydrous conditions into another round bottom flask and to it was added a solution of 5'-O-DMT-3'-O-acetyl-2'-deoxyguanosine (1 mmole) in anhydrous tetrahydrofuran (50 mL). After stirring for 6–8 hours, the reaction was quenched with triethylammonium bicarbonate solution (50 mL). The reaction mixture was concentrated, taken up in ethyl acetate (200 mL) and washed with brine (50 mL). Drying ($Na_2SO_4$) followed by concentration and purification by flash silica gel chromatography afforded the desired product as a colorless product.

Example 10

Loading of N-Protected-5'-O-DMT-3'-O-acetyl-2'-deoxyguanosine on HL 30 Primer Solid Support Loading of the protected nucleoside was performed under the standard conditions using amino derivatized primer support purchased from Amhersham-Pharmacia Biotech. Amino derivatized HL 30 Primer support, Hunig's base (12 equiv), HBTU activator (4 equiv), the DMT dG nucleoside with the linker synthesized as above and anhydrous acetonitrile (100 mL) were taken in a round bottom flask and closed and shaken mechanically at room temperature for 6 hours. The support was then washed with acetonitrile (100 mL) and dried. Then a mixture of Cap A and Cap B solution used for oligomerization (20 mL each) was added to the support followed by a catalytic amount of 4-dimethylaminopyridine and shaken overnight mechanically. The support was washed with acetonitrile (200 mL), anhydrous DMF (100 mL), methanol (100 mL) and finally with anhydrous ether (200 mL) The support was finally dried thoroughly and then tested for loading.

Example 11

Synthesis of Fully-modified 5'-d(TCC-GTC-ATC-GCT-CCT-CAG-GG)-3' (SEQ ID NO:2) Phosphorothioate 20-mer The synthesis of above sequence was performed on a Pharmacia OligoPilot I1 Synthesizer on a 160 μmole scale using the cyanoethyl phosphoramidites obtained from Pharmacia and Pharmacia's HL 30 primer support loaded with DMT-N6bz-dG nucleoside (support linked to 3'-position). Detritylation was performed using 3% dichloroacetic acid in toluene (volume/volume). Activation of phosphoramidites was done with a 0.4M solution of 1H-tetrazole in acetonitrile. Sulfurization was performed using a 0.2M solution of phenylacetyl disulfide in acetonitrile:3-picoline (1:1 v/v) for 2 minutes. At the end of synthesis, the support was washed with a solution of triethylamine in acetonitrile (1:1, v/v) for 12 h, and treated with $NH_4OH$ (30%) for 15 hours at 60° C., filtered, rinsed with ethanol/water (1/1, v/v), and the combined solutions were evaporated to dryness under vacuum. The residue was dissolved in water (50 mL). Purification of oligonucleotides by reversed phase high performance liquid chromatography (RP-HPLC) was performed on a Waters Nova-Pak C18 column (3.9×300 mm) using a Waters HPLC system (600E System Controller, 996 Photodiode Array Detector, 717 Autosampler). For analysis an acetonitrile (A)/0.1M triethylammonium acetate gradient was used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR(DMT-off) 10–11 min, tR(DMT-on) 14–16 min.

The DMT-on fractions were collected and was evaporated in vacuum, redissolved in water and the DMT group removed. An aliquot (30 μL) was transferred into an Eppendorff tube (1.5 mL), and acetic acid (50%, 30 μL) was added. After 30 min at room temperature sodium acetate (2.5M, 20 μL) was added, followed by cold ethanol (1.2 mL). The mixture was vortexed and cooled in dry ice for 20 min. The precipitate was spun down with a centrifuge, the supernatant was discarded and the precipitate was rinsed with ethanol and dried under vacuum to give the deprotected product.

Example 12

Synthesis of Fully-modified 5'-d(TCC-GTC-ATC-GCT-CCT-CAG-GG)-3' (SEQ ID NO:2) Phosphorothioate 20-mer Using dG Functionalized Solid Support Linked Through the N2 Amino Group The synthesis of the above sequence was performed on a Pharmacia OligoPilot I1 Synthesizer on a 140 μmole scale using the cyanoethyl phosphoramidites obtained from Pharmacia and Pharmacia's HL 30 primer support loaded with 5'-O-DMT-3'-O-acetyl-N2-dodecanoyl-dG nucleoside. Detritylation was performed using 3% dichloroacetic acid in toluene (volume/volume). Activation of phosphoramidites was done with a 0.4M solution of 1H-tetrazole in acetonitrile. Sulfurization was performed using a 0.2M solution of phenylacetyl disulfide in acetonitrile:3-picoline (1:1 v/v) for 2 minutes. At the end of synthesis, the support was washed with a solution of triethylamine in acetonitrile (1:1, v/v) for 12 h, and treated with $NH_4OH$ (30%) for 15 hours at 60° C., filtered, rinsed with ethanol/water (1/1, v/v), and the combined solutions were evaporated to dryness under vacuum. The residue was dissolved in water (50 mL). Purification of oligonucleotides by reversed phase high performance liquid chromatography (RP-HPLC) was performed on a Waters Nova-Pak C18 column (3.9×300 mm) using a Waters HPLC system (600E System Controller, 996 Photodiode Array Detector, 717 Autosampler). For analysis an acetonitrile (A)/0.1M triethylammonium acetate gradient was used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR(DMT-off) 10–11 min, tR(DMT-on) 14–16 min.

The DMT-on fractions were collected and was evaporated in vacuum, redissolved in water and the DMT group removed. An aliquot (30 μL) was transferred into an Eppendorff tube (1.5 mL), and acetic acid (50%, 30 μL) was added. After 30 min at room temperature sodium acetate (2.5M, 20 μL) was added, followed by cold ethanol (1.2 mL). The mixture was vortexed and cooled in dry ice for 20 min. The precipitate was spun down with a centrifuge, the supernatant was discarded and the precipitate was rinsed with ethanol and dried under vacuum to give the deprotected product.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method of preparing an oligomeric compound having at least one moiety of formula:

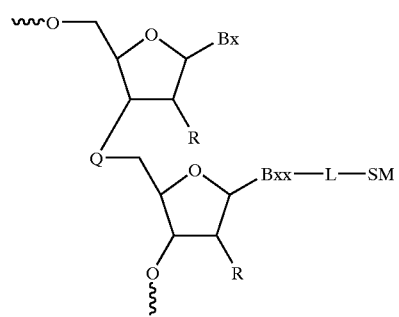

wherein:
Q is an internucleoside linkage;
Bx is an optionally blocked heterocyclic base moiety;
Bxx is a purine or purine analog;
each R is, independently, hydrogen or an optionally protected substituent group;
L is a bifunctional linking moiety having the formula —C(=O)—(CH$_2$)$_{nn}$—C(=O)— where nn is from 4 to 25; and
SM is a support medium;
comprising the steps of:
(a) providing a compound of formula:

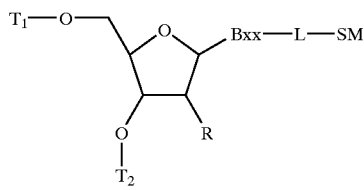

wherein:
T$_1$ is a 5'-hydroxyl protecting group; and
T$_2$ is a hydroxyl blocking group, a nucleoside, a nucleotide, an oligonucleoside, an oligonucleotide or a conjugate group;
(b) removing said 5'-hydroxyl protecting group to form a deprotected hydroxyl group by contacting same with a reagent effective to remove said protecting group;

(c) treating said deprotected hydroxyl group with a further compound having the formula:

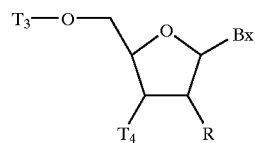

wherein:
T$_3$ is a 5'-hydroxyl protecting group, a nucleoside, a nucleotide, an oligonucleoside, an oligonucleotide or a conjugate group; and
T$_4$ is a reactive P$^{III}$ species for forming an internucleoside linkage;
and an activating agent for a time and under conditions effective to form an extended oligomeric compound;
d) treating said extended oligomeric compound with a capping agent to form a capped compound;
e) treating said capped compound with an oxidizing agent; and
f) optionally repeating steps b through e one or more additional cycles to form said oligomeric compound.

2. The method of claim 1 further comprising treating said oligomeric compound with a reagent effective to form a deblocked oligomeric compound.

3. The method of claim 2 wherein said reagent is effective to cleave said ligomeric compound from the support medium.

4. The method of claim 2 further comprising treating said deblocked ligomeric compound with a reagent effective to cleave said oligomeric compound from the support medium.

5. The method of claim 2 wherein said deblocking reagent is a basic solution.

6. The method of claim 5 wherein said basic solution is concentrated ammonium hydroxide.

7. The method of claim 1, wherein said T$_3$ is said 5'-hydroxyl protecting group, further comprising treating said oligomeric compound with a reagent effective to deprotect said 5'-hydroxyl protecting group to give a free hydroxyl group.

8. The method of claim 1 wherein said activating agent is 1-H-tetrazole.

9. The method of claim 1 wherein said oxidizing agent is an oxaziridine.

10. The method of claim 9 wherein said oxidizing agent is 10-camphorsulphonyl oxazaridine, 2-phenylsulphonyl-3- phenyl oxazaridine, 2-(phenylsulphonyl)-3-(3-nitrophenyl) oxazaridine, or 8,8-dihalo-10-camphorsulphonyl oxazaridine.

11. The method of claim 1 wherein said reactive $P^{III}$ species is a phosphoramidite.

12. The method of claim 1 wherein said heterocyclic base moiety is adeninyl, $N^6$-benzoyladeninyl, 2-aminoadeninyl, cytosinyl, $N^4$-benzoylcytosinyl, 5-methylcytosinyl, $N^4$-benzoyl-5-methylcytosinyl, thyminyl, uracilyl, guaninyl or $N^2$-isobutyrylguaninyl.

13. The method of claim 1 wherein said oligomeric compound comprises from about 10 to about 30 monomer subunits.

14. The method of claim 1 wherein said oligomeric compound comprises from about 15 to 25 monomer subunits.

15. The method of claim 1 wherein nn is from 6 to 20.

16. The method of claim 1 wherein nn is from 8 to 16.

17. The method of claim 1 wherein the bifunctional linking moiety attaches the support medium to the oligomeric compound at a heterocyclic base functional group.

18. The method of claim 17 wherein said functional group is a primary or secondary amino group.

19. The method of claim 17 wherein said functional group is a primary amino group.

20. The method of claim 1 wherein said internucleoside linkage is phosphodiester, phosphorothioate, chiral phosphorothioate, phosphorodithioate, phosphoramidate or alkylphosphonate (—O—P(jj)(O)—O—) where jj is $C_1$–$C_{12}$ alkyl.

21. The method of claim 1 wherein said oligomeric compound comprises from about 5 to about 50 monomer subunits.

22. The method of claim 1 wherein $T_2$ is a hydroxyl blocking group.

23. The method of claim 22 wherein said hydroxyl blocking group is base labile.

24. The method of claim 22 wherein said hydroxyl protecting group is of the formula —C(=O)$R_d$ where $R_d$ is $C_1$ to $C_{12}$ alkyl.

25. The method of claim 24 wherein $R_d$ is $CH_3$.

26. The method of claim 1 wherein each said substituent group R is, independently, hydroxyl, $C_1$–$C_{20}$ alkyl, $C_2$–$C_{20}$ alkenyl, $C_2$–$C_{20}$ alkynyl, halogen, amino, thiol, keto, carboxyl, nitro, nitroso, nitrile, trifluoromethyl, trifluoromethoxy, O-alkyl, O-alkenyl, O-alkynyl, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, imidazolyl, azido, hydrazino, hydroxylaamino, isocyanato, reporter molecule, conjugate, polyamine, polyamide, polyalkylene glycol, or polyether;

or each substituent group has one of formula I or II:

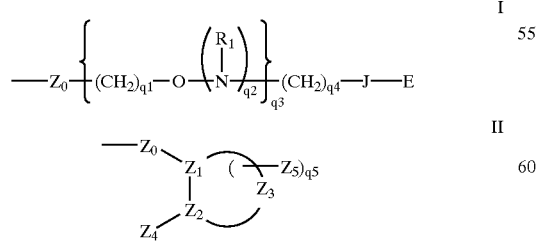

wherein:
$Z_0$ is O, S or NH;
J is a single bond, O or C(=O);

E is $C_1$–$C_{10}$ alkyl, $N(R_1)(R_2)$, $N(R_1)(R_5)$, $N=C(R_1)(R_2)$, $N=C(R_1)(R_5)$ or has formula IV;

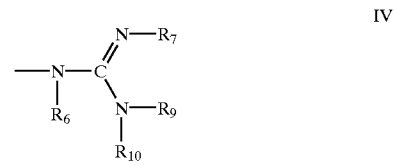

each $R_6$, $R_7$, $R_9$ and $R_{10}$ is, independently, hydrogen, $C(O)R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—$L_1$,
T is a bond or a linking moiety;
$L_1$ is a conjugate group or a solid support material;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group;

each $R_3$ and $R_4$ is, independently, H, $C_1$–$C_{10}$ alkyl, a nitrogen protecting group, or $R_3$ and $R_4$, together, are a nitrogen protecting group;

$Z_4$ is OX, SX, or $N(X)_2$;
each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;

$R_5$ is H or $C_1$–$C_8$ alkyl;

$Z_1$, $Z_2$ and $Z_3$ form a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$, $OR_1$, halo, $SR_1$ or CN;

each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and provided that when $q_3$ is 0, $q_4$ is greater than 1.

27. A method of preparing an oligomeric compound of formula:

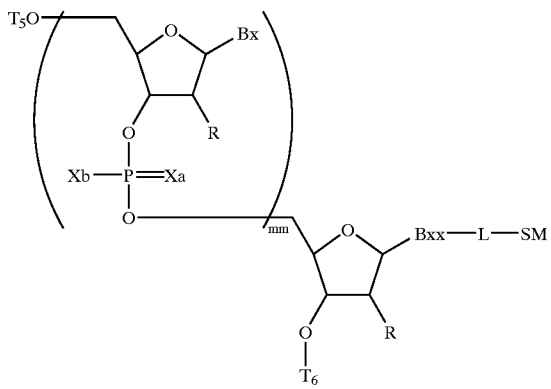

wherein:
T$_5$ is H, a hydroxyl blocking group, a nucleoside, an oligonucleoside, a nucleotide an oligonucleotide or a conjugate group;
T$_6$ is H, a hydroxyl protecting group, a nucleoside, an oligonucleoside, a nucleotide an oligonucleotide or a conjugate group;
mm is from about 5 to about 50;
each Xa is, independently, O or S;
each Xb is, independently, OH, SH or NR$_a$R$_b$;
each R$_a$ and R$_b$ is, independently, H, a nitrogen protecting group, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, wherein said substitution is by hydroxyl, amino, alkoxy, carboxy, benzyl, phenyl, nitro, thiol, thioalkoxy, halogen, alkyl, aryl, alkenyl or alkynyl;
Bxx is a purine or purine analog;
each Bx is, independently, an optionally blocked heterocyclic base moiety;
each R is, independently, hydrogen or an optionally protected substituent group;
L is a bifunctional linking moiety having the formula —C(=O)—(CH$_2$)$_{nn}$—C(=O)— where nn is from 4 to 25; and
SM is a support medium;
comprising the steps of:
(a) providing a compound of the formula:

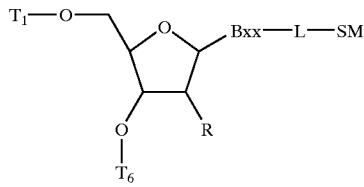

wherein:
T$_1$ is a 5'-hydroxyl protecting group;
(b) removing said 5'-hydroxyl protecting group to form a deprotected hydroxyl group by contacting same with a reagent effective to remove said protecting groups;
(c) treating said deprotected hydroxyl group with a further compound having the formula:

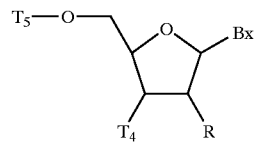

wherein:
T$_4$ is a phosphoramidite;
and an activating agent for a time and under conditions effective to form an extended oligomeric compound;
d) treating said extended oligomeric compound with a capping agent to form a capped compound;
e) treating said capped compound with an oxidizing agent; and
f) optionally repeating steps b through e one or more times to form said oligomeric compound.

28. The method of claim 27 wherein each substituent group R is, independently, hydroxyl, C$_1$–C$_{20}$ alkyl, C$_2$–C$_{20}$ alkenyl, C$_2$–C$_{20}$ alkynyl, halogen, amino, thiol, keto, carboxyl, nitro, nitroso, nitrile, trifluoromethyl, trifluoromethoxy, O-alkyl, O-alkenyl, O-alkynyl, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, imidazolyl, azido, hydrazino, hydroxylamino, isocyanato, reporter molecule, conjugate, polyamine, polyamide, polyalkylene glycol, or polyether;
or each substituent group has one of formula I or II:

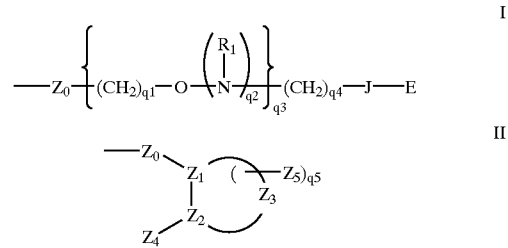

wherein:
Z$_0$ is O, S or NH;
J is a single bond, O or C(=O);
E is C$_1$–C$_{10}$ alkyl, N(R$_1$)(R$_2$), N(R$_1$)(R$_5$), N=C(R$_1$)(R$_2$), N=C(R$_1$)(R$_5$) or has formula IV;

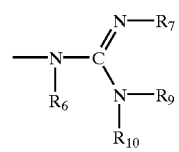

each R$_6$, R$_7$, R$_9$ and R$_{10}$ is, independently, hydrogen, C(O)R$_{11}$, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, alkylsulfonyl, arylsulfonyl, or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, R$_9$ and R$_{10}$, together form a phthalimido moiety with the nitrogen atom to which they are attached;

each $R_{11}$, is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—$L_1$,

T is a bond or a linking moiety;

$L_1$ is a conjugate group or a solid support material;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group;

each $R_3$ and $R_4$ is, independently, H, $C_1$–$C_{10}$ alkyl, a nitrogen protecting group, or $R_3$ and $R_4$, together, are a nitrogen protecting group;

$Z_4$ is OX, SX, or $N(X)_2$;

each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;

$R_5$ is H or $C_1$–$C_8$ alkyl;

$Z_1$, $Z_2$ and $Z_3$ form a ring system having from about 4 to about 7, carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

29. The method of claim 27 further comprising treating said oligomeric compound with a reagent effective to form a deblocked oligomeric compound.

30. The method of claim 29 wherein said reagent is effective to cleave said oligomeric compound from the support medium.

31. The method of claim 29 further comprising treating said deblocked oligomeric compound with a reagent effective to cleave said oligomeric compound from the support medium.

32. The method of claim 27 wherein said deblocking reagent is a basic solution.

33. The method of claim 32 wherein said basic solution is concentrated ammonium hydroxide.

34. The method of claim 27, wherein said $T_5$ is said 5'-hydroxyl protecting group, further comprising treating said oligomeric compound with a reagent effective to deprotect said 5'-hydroxyl protecting group.

35. The method of claim 27 wherein said activating agent is 1-H-tetrazole.

36. The method of claim 27 wherein said oxidizing agent is an oxaziridine.

37. The method of claim 36 wherein said oxidizing agent is 10-camphorsulphonyl oxazaridine, 2-phenylsulphonyl-3-phenyl oxazaridine, 2-(phenylsulphonyl)-3-(3-nitrophenyl) oxazaridine, or 8,8-dihalo-10-canphorsulphonyl oxazaridine.

38. The method of claim 27 wherein said heterocyclic base moiety is adeninyl, $N^6$-benzoyladeninyl, 2-aminoadeninyl, cytosinyl, $N^4$-benzoylcytosinyl, 5-methylcytosinyl, $N^4$-benzoyl-5-methylcytosinyl, thyminyl, uracilyl, guaninyl or $N^2$-isobutyrylguaninyl.

39. The method of claim 27 wherein nn is from 6 to 20.

40. The method of claim 27 wherein nn is from 8 to 16.

41. The method of claim 27 wherein the covalent attachment of the bifunctional linking moiety to said Bxx is through an amide bond formed between an exocyclic amino group on Bxx and an acyl group on said bifunctional linking moiety.

42. The method of claim 41 wherein Bxx is a purine.

43. The method of claim 41 wherein Bxx is a purine analog.

44. The method of claim 43 wherein said purine analog is xanthine, hypoxanthine, 2-aminoadenine, 7-methylguanine, 7-methyladenine, a 6-methyl derivative of adenine or guanine, a 2-propyl derivative of adenine or guanine, an 8-halo, 8-amino, 8-thiol, 8-thioalkyl, or an 8-hydroxyl substituted adenine or guanine, 8-azaguanine, 8-azaadenine, 7-deazaguanine, 7-deazaadenine, 3-deazaguanine, or 3-deazaadenine.

45. The method of claim 44 wherein said purine analog has a primary or secondary amino functionality integral with or exocyclic to the purine ring system.

46. The method of claim 27 wherein $T_6$ is said hydroxyl protecting group.

47. The method of claim 46 wherein said hydroxyl protecting group is base labile.

48. The method of claim 46 wherein said hydroxyl protecting group is of the formula —C(=O)$R_d$ where $R_d$ is $C_1$ to $C_{12}$ alkyl.

49. The method of claim 48 wherein $R_d$ is $CH_3$.

50. The method of claim 27 wherein mm is from about 10 to about 30.

51. The method of claim 27 wherein mm is from about 15 to 25.

52. The method of claim 27 wherein said support medium is an insoluble solid support.

53. The method of claim 27 wherein said support medium is a soluble polymeric support.

54. The method of claim 53 wherein said polymeric support is monomethoxy polyethylene glycol.

55. The method of claim 54 wherein said polymeric support is poly(N-acryloyl-morpholine).

56. The method of claim 27 wherein said purine analog is xanthine, hypoxanthine, 2-aminoadenine, 7-methylguanine, 7-methyladenine, a 6-methyl derivative of adenine or guanine, a 2-propyl derivative of adenine or guanine, an 8-halo, 8-amino, 8-thiol, 8-thioalkyl, or an 8-hydroxyl substituted adenine or guanine, 8-azaguanine, 8-azaadenine, 7-deazaguanine, 7-deazaadenine, 3-deazaguanine, or 3-deazaadenine.

57. The method of claim 56 wherein said purine analog has a primary or secondary amino functionality integral with or exocyclic to the purine ring system.

* * * * *

UNITED STATES PATENT AND TRADEMARK OFFICE
CERTIFICATE OF CORRECTION

PATENT NO.    : 6,649,750 B1
DATED         : November 18, 2003
INVENTOR(S)   : Daniel C. Capaldi et al.

It is certified that error appears in the above-identified patent and that said Letters Patent is hereby corrected as shown below:

Title page,
Item [56], References Cited, OTHER PUBLICATIONS, "Barbato et al.," reference, please delete "Necleotide" and insert therefore -- Nucleotide --;
"Barbato et al.," reference, please delete "Oligonucleotides" and insert therefore -- Oligodeoxynucleotides --;

Column 30,
Lines 48 and 51, please delete "ligomeric" and insert therefore -- Oligomeric --;

Column 31,
Line 50, please delete "hydroxylaamino" and insert therefore -- hydroxylamino --.

Signed and Sealed this

Thirteenth Day of July, 2004

JON W. DUDAS
*Acting Director of the United States Patent and Trademark Office*